US007168636B2

(12) United States Patent
Lebeda et al.

(10) Patent No.: US 7,168,636 B2
(45) Date of Patent: Jan. 30, 2007

(54) APPARATUS, METHOD AND SYSTEM FOR APPLYING SUBSTANCES TO FORAGE, GRAIN, AND HARVESTED CROPS

(75) Inventors: Joseph R. Lebeda, Des Moines, IA (US); James M. Oepping, Wilton, IA (US); Jeffrey S. Roberts, Hudson, WI (US)

(73) Assignee: Pioneer Hi-Bred International, Inc., Johnston, IA (US)

(*) Notice: Subject to any disclaimer, the term of this patent is extended or adjusted under 35 U.S.C. 154(b) by 0 days.

(21) Appl. No.: 10/899,785

(22) Filed: Jul. 27, 2004

(65) Prior Publication Data

US 2005/0077389 A1 Apr. 14, 2005

Related U.S. Application Data

(63) Continuation-in-part of application No. 10/627,227, filed on Jul. 28, 2003, now abandoned.

(51) Int. Cl.

| | |
|---|---|
| ***B05B 1/34*** | (2006.01) |
| *B05B 17/04* | (2006.01) |
| *B05B 7/08* | (2006.01) |

(52) U.S. Cl. ............................ 239/389; 239/11; 239/8; 239/311; 239/310; 239/349; 239/351; 239/366; 239/469; 239/172; 239/499; 417/42; 417/22

(58) Field of Classification Search .................. 239/77, 239/469, 122, 499, 311, 314, 310, 349, 351, 239/366; 471/42; 417/22

See application file for complete search history.

(56) References Cited

U.S. PATENT DOCUMENTS 827,174 A * 7/1906 Patterson ..................... 239/77

(Continued)

FOREIGN PATENT DOCUMENTS

EP 1581049 B1 3/2006

(Continued)

OTHER PUBLICATIONS

Abstract of FR 2 851 941, from http://sughrue.patentfetcher.com/Patent-Fetcher.php?PN=FR2851941 (1 page).

(Continued)

*Primary Examiner*—David A. Scherbel
*Assistant Examiner*—James S. Hogan
(74) *Attorney, Agent, or Firm*—McKee, Voorhees & Sease, P.L.C.

(57) ABSTRACT

An apparatus, method and system for applying a biologically active or chemical substance to a relatively large volume harvested or pre-harvested crop includes relatively small container of a mixture biologically active or chemical substance and water in fluid communication with fluid conduit. A pump moves mixture from the bottle through the conduit. A source of pressurized air is in fluid communication with the conduit to aerate the mixture. The aerated mixture is expelled through a nozzle at distal end of the conduit. In one aspect, the controller can monitor speed of the pump by monitoring operating voltage of the pump. Speed of the pump can be adjusted to adjust application rate. In one aspect, a process combines a flow of air through an orifice with the metering of a low volume of additive, such as an aid to preservation, to a crop as it is being cut or harvested to provide for even distribution of the additive to the crop.

35 Claims, 8 Drawing Sheets

U.S. PATENT DOCUMENTS

| | | | | |
|---|---|---|---|---|
| 1,218,953 | A * | 3/1917 | Oldham | 222/129 |
| 3,472,454 | A * | 10/1969 | Horton et al. | 239/77 |
| 3,618,856 | A * | 11/1971 | Sachnik | 239/8 |
| 3,841,555 | A | 10/1974 | Lilja | |
| 3,917,168 | A * | 11/1975 | Tenney | 239/13 |
| 4,182,491 | A * | 1/1980 | Parke et al. | 239/11 |
| 4,220,998 | A | 9/1980 | Kays | |
| 4,392,611 | A | 7/1983 | Bachman et al. | |
| 4,500,228 | A | 2/1985 | McDonald et al. | |
| 4,542,855 | A | 9/1985 | Stacey | |
| 4,723,709 | A | 2/1988 | Curran, Jr. et al. | |
| 4,778,749 | A | 10/1988 | Vasington et al. | |
| 5,248,448 | A * | 9/1993 | Waldron et al. | 516/6 |
| 5,667,806 | A | 9/1997 | Kantor | |
| 5,718,377 | A | 2/1998 | Tedders et al. | |
| 5,884,846 | A | 3/1999 | Tan | |
| 5,931,882 | A | 8/1999 | Fick et al. | |
| 6,206,300 | B1 | 3/2001 | Roudebush et al. | |
| 6,327,889 | B1 | 12/2001 | Seltzer et al. | |
| 6,443,369 | B1 | 9/2002 | Dohrmann et al. | |
| 6,696,382 | B1 | 2/2004 | Zelenay et al. | |
| 6,848,627 | B2 | 2/2005 | Oepping et al. | |
| 2002/0122827 | A1 | 9/2002 | Platz et al. | |
| 2002/0124541 | A1 * | 9/2002 | Oepping et al. | 56/16.4 R |
| 2003/0046859 | A1 | 3/2003 | Robinson, Jr. | |
| 2003/0201333 | A1 | 10/2003 | Oepping | |

FOREIGN PATENT DOCUMENTS

| | | | |
|---|---|---|---|
| FR | 2 519 053 | A1 | 7/1983 |
| FR | 2 519 053 | B3 | 7/1983 |
| FR | 2677217 | A1 | 12/1992 |
| FR | 2 851 941 | A1 | 5/2005 |
| GB | 2244903 | A | 12/1991 |
| WO | PCT/NL94/00041 | | 2/1994 |
| WO | 97 16257 | A1 | 5/1997 |
| WO | PCT/9958253 | | 11/1999 |
| WO | PCT/US03/12592 | | 4/2003 |

OTHER PUBLICATIONS

"Apparatus Test Report of the Biological Federal Institute for Agricultural and Forrestry" (Biologischen Bundesanstalt Fur Land- und Forstwirtschaft) Braunschweig No. G 1321, concerning Moist Dressing Apparatus Goldsaat GBS-3/F-A; bearing Oct. 17, 1990 date. (4 pages).

English translation of text of "Apparatus Test Report of the Biological Federal Institute for Agricultural and Forrestry" (Biologischen Bundesanstalt Fur Land- und Forstwirtschaft) Braunschweig No. G 1321, concerning Moist Dressing Apparatus Goldsaat GBS-3/F-A; bearing Oct. 17, 1990 date. 5 pages.

Brochure relating to Goldsaat Apparatus Moist dresserGBS 3/F-A, estimated publication date of no later than approximately Jul. 1993. (2 pages).

English translation of text of brochure relating to Goldsaat Apparatus Moist dresser GBS 3/F-A, estimated publication date of no later than approximately Jul. 1993. (2 pages).

Metering Instructions for Goldsaat Moist Dressing Type GBS 3/F-A, estimated publication date of no later than approximately the early 1990's. (19 pages).

English translation of text of Metering Instructions for Goldsaat Moist Dressing Device Type GBS 3/F-A, estimated publication date no later than approximately the early 1990's. (18 pages).

Instructions for operation and appendix for Ultra-Exact Metering Device Weda Model UED2 by Weda-Dammann & Westerkamp GmbH, estimated publication date of no later than approximately Jul. 27, 2004 (7 pages).

English translation of text of Instructions for operation and appendix for Ultra-Exact Metering Device Weda Model UED2 by Weda-Dammann & Westerkamp GmbH, estimated publication date of no later than approximately Jul. 27, 2004, (7 pages).

Information notice regarding Model UED2 by Weda, estimated publication date of no later than approximately Jul. 9, 2004 (1 page).

English translation of text of Information notice regarding Model UED2 by Weda, estimated publication date of no later than approximately Jul. 9, 2004 (1 page).

* cited by examiner

APPARATUS, METHOD AND SYSTEM FOR APPLYING SUBSTANCES TO FORAGE, GRAIN, AND HARVESTED CROPS

RELATION TO RELATED APPLICATIONS

This application, under 35 U.S.C. §§ 119 and/or 120, claims priority to and the benefit of, and is a Continuation-in-Part of, U.S. patent application Ser. No. 10/627,227 filed Jul. 28, 2003 now abandoned, entitled "A PROCESS FOR APPLYING ADDITIVES TO CROPS DURING HARVEST USING COMPRESSED AIR TO DISTRIBUTE THE ADDITIVE EVENLY ON THE CROP".

INCORPORATION BY REFERENCE

The contents of co-owned, co-pending U.S. patent applications Ser. No. 10/140,596 filed May 7, 2002, and Ser. No. 10/627,227 filed Jul. 28, 2003, entitled "A PROCESS FOR APPLYING ADDITIVES TO CROPS DURING HARVEST USING COMPRESSED AIR TO DISTRIBUTE THE ADDITIVE EVENLY ON THE CROP", are incorporated by reference herein in their entirety. The contents of U.S. Pat. No. D409,303, issued May 4, 1999 and PCT publication WO 99/58253, published Nov. 18, 1999, are incorporated by reference herein in their entirety.

I. BACKGROUND OF THE INVENTION

A. Field of the Invention

The present invention relates to application of a biologically active or chemical substance to relatively large volumes of target product, one example being pre-harvested or harvested crop, and in particular, to an apparatus, method, and system of applying biologically active or chemical substance in a minute ratio to the target product, whether it is moving relative to the substance, the substance is moving relative to it, or both.

B. Problems in the Art

It is many times desirable to treat harvested agricultural crop by applying substance having, at least in part, some biologically active organisms. One primary example is a forage inoculant which contains bacteria that, when applied in appropriate concentration to harvested agricultural crop, can reduce rate of degradation of the harvested agricultural crop.

In the example of forage inoculant, a relatively small concentration of inoculant can effectively treat a relatively large volume of harvested crop. For example, ratios on the order of 40 grams of inoculant to 50 tons of harvested crop are typical. However, relatively effective even application of such small quantities to such large quantities of agricultural crop is not a trivial matter, particularly if the crop or the applicator, or both, are moving relative to one another.

Additives are in common use for purposes of aiding in the preservation of the crop during storage. Two types of additives are the most common: (1) acid to reduce bacterial activity and, (2) inoculants to add favorable activity. These additives must be applied at time of harvest to provide the maximum benefit in the aid to preservation of the crop. Harvesting of the crop takes place over a large area through the use of mobile harvesting equipment such as forage harvesting and baling implements. These implements have been designed for maximum speed in harvesting with very little consideration of being compatible with the requirements of applying the additives used to aid in the preservation of the crop. The carrying capacity of harvesting equipment for additives being used is sometimes limited to small amounts of material. In such cases, it is beneficial to use additives that require the lowest ratio of additive to crop so, with limited carrying capacity, the harvesting implement is not stopping to refill small reservoirs for the additives on a frequent basis.

Additives to aid in the preservation of crops have been developed with increasing lower ratios of application in recent years. High-strength acid formulas have been introduced that are effective in controlling bacterial growth when applied at ratios a low as 0.005% of the crop being treated. Highly concentrated inoculants have been developed that are effective at rates as low as 0.001% of the crop being treated. These low inclusion rate products have reduced the need to stop and fill the reservoirs on the harvesting implements.

The problem that arises with the products that have low rates of application is attaining even coverage over the complete crop being treated. To be effective on the entire crop, coverage of these additives must be even on the entire crop. For liquids, conventional spray techniques are less than effective at these low rates.

One current method of inoculant application premixes concentrated inoculant with water in a large tank (e.g. 1:200 to 1:3000 ratio inoculant to water). Such tanks can hold, sometimes, on the order of 100 or more gallons of water. A conventional spraying system is then used to spray the mixture on the harvested crop. It is cumbersome and time consuming to mix, carry, and replenish such a large volume. It can also be wasteful of inoculant, which is biologically active and not inexpensive. Careful pre-mixing must take place. Sufficient power and fuel must be used to manipulate a tank of such size and weight. If the full tank of mixture is not used, the remainder most times must be thrown away. There is no practical way to store the mixture. Additionally, a relatively accurate spraying system must be used. The whole system usually must be taken back to a base location to refill and remix the tank. Such a spraying system uses a substantial amount of water per unit forage.

An alternative method was developed to address some of the aforementioned problems and deficiencies. The APPLI-PRO™ system available from Pioneer Hi-Bred International, Des Moines, Iowa, and disclosed at U.S. Ser. No. 10/140,596 and WO 99/58253, instead uses a palm or hand-sized APPLI-PRO™ container or bottle (see U.S. Pat. No. D409,303) of concentrated inoculant pre-mix that could be removably installed to its spraying system. A larger water tank is in fluid communication with a first pump, which pumps water from the tank at a desired rate to spray nozzles. A second pump, preferably an injection pump, is in fluid communication with the small inoculant concentration bottle and the fluid conduit. Precise, adjustable operation of the injection pump served as a precise metering of concentrated inoculant into the main water stream to the sprayers. This eliminated the requirement of pre-mixing in the large water tank. It allowed for dispensing of only the needed amount of inoculant. At the end of a spraying session, the inoculant bottle could either be exchanged or any remainder sealed and stored in that container, and then available for subsequent use. The system provides accurate, efficient utilization of inoculant with reduced margin of error. It is also highly adjustable for different needs. However, it requires two separate pumping mechanisms. Additionally, it still uses a substantially large holding tank for the water supply if large quantities of agricultural crop were to be sprayed in one session.

Other attempts have been made at improved forage inoculant-type application systems. In the ULV™ model, available from Pioneer Hi-Bred International, instead of a large water tank, either as a pre-mix tank or water supply tank, again a much smaller single container (e.g. 2.5 liters) contains the pre-mix of inoculant and water. Also, instead of spraying a ratio of a very small amount of inoculant to large amounts of water an atomizer is used to atomize the mixture in a very accurate, consistent manner to apply the right amount on the harvested forage. However, it has been found that an effective atomizer is relatively expensive, and that the overall apparatus can cost several thousands of dollars.

Therefore, additional room for improvement in the art still exists. A more economical, less cumbersome, efficient and effective application system is needed. Other factors must be considered in designing systems to apply such types of substances.

First, many biologically active substances have some threshold of tolerance for trauma. For example, some pumps and nozzles that try to atomize fluid many times subject the living cells to shearing forces that can damage their cells. Of course, damaged inoculant cells can inhibit or destroy their efficacy.

Secondly, care must be taken to avoid over-drying the biologically active substance, either while stored, awaiting application, or during application. Excessive drying or exposure to air can also reduce the efficacy of the biological ingredient.

Third, even with the specific example of forage inoculants, there are a wide variety of environments in which the inoculant could be applied and environmental factors could affect application. For example, it could be applied on a harvested crop moving past a spray device on some sort of an exposed conveyor. Care must be taken to direct the inoculant in an even manner on the moving crop. Conveyance equipment is becoming more and more sophisticated. The crop can be moving at substantial speeds and volumes. An inoculant application system must be able to be adjusted and adapted accordingly. For example, the application system might be carried on-board a harvesting device. Inoculant application may be made at or near the internal conveying systems, e.g. mechanical or pneumatic, of the machine. The speed the crop moves can be high; for example, over a hundred miles an hour. With exposed conveyors or internal conveyors, the effect of wind or vacuum on an airborne mixture created by high-speed venturi effect must be handled.

On the other hand, as detailed in Ser. No. 10/140,596 and WO 99/58253, there are other instances where the application system may be moving relative to the harvested crop, or both the sprayer and the crop moving. An effective application system must be able to handle those environments.

For purposes of this description, the term “target product” will be used to refer to any material, living or not, or any surface to which the apparatus, system or method of the present invention could be used to apply a biologically active or chemical substance in a liquid pre-mix form. For purposes of this description, the term “crop” will be used to refer to an example of a target product, and includes any plant material, whether pre-harvested (e.g. growing in a field or cut but without the desired part being yet harvested), or during and after harvesting.

II. SUMMARY OF THE INVENTION

It is therefore a principal object, feature, advantage, and/or aspect of the present invention to provide an apparatus, method, or system of applying a biologically active or chemical substance in relatively small quantities to relatively large volumes of a target product that improves over or solves problems and deficiencies in the art.

Additional objects, features, aspects, and/or advantages of the present invention include an apparatus, method, or system for applying a biologically active or chemical substance in relatively small amounts to relatively large volumes of a target product which:

a. is economical:

b. reduces the amount of carrier fluid that must be available or carried to mix with the biologically active or chemical substance;

c. is adaptable to work with up to extremely large volumes and rates of volume flow of target product, including crops;

d. avoids trauma on the biologically active or chemical substance;

e. is adapted for high throughput of target product;

f. is accurate;

g. is adjustable for different volumes and speeds of different target products;

h. is consistent and even in application;

i. is durable;

j. provides relatively easy maintenance and repairs;

k. is adaptable for a variety of placements, environments, and functions;

l. provides an even mix and application by air assist.

These and other objects, features, aspects, and/or advantages of the present invention will become more apparent with reference to the accompanying specification and claims.

One particular aspect of the present invention includes an apparatus, method, and system for applying a biologically active or chemical substance to a relatively large volume of target product, including crop. The biologically active or chemical substance is mixed with water. The mixture is contained in a relatively small, hand carryable container or bottle which can be placed in fluid communication with a conduit to a nozzle with spraying end. A pump is adapted to move the mixture from the bottle through the conduit towards the nozzle. Pressurized air is mixed with the mixture in the conduit to aerate the mixture. The pump is controllable and adjustable to vary the rate of application of the mixture from the nozzle. The nozzle, pump, and pressurized air are selected to essentially mist the mixture in a controlled, even, consistent manner, minimizing trauma on any biologically active or chemical ingredients. What might be called the “air assist” promotes an even discharge and application. A relatively low volume of liquid mixture is precisely metered onto the target product with a relatively large volume of pressurized air. The primary components of the system can be integrated into a relatively small-sized unit.

In another aspect of the invention, a process employs a stream of air under pressure to deliver low rates of additives to crops, so that the air distributes the additive to the crop evenly. The additive being applied, e.g. at ratios under 2% of the crop being treated, is thus evenly distributed, leading to more effective response to the additive.

In another aspect of the invention, voltage of the pump motor is monitored. Adjustment of the voltage to the pump can then adjust the output of the system.

In another aspect of the invention, the nozzle and aeration of the mixture cooperate with the pumping of the mixture to create a consistent, controlled spray or distribution without shearing action which can be harmful to the biologically active or chemical substance.

Another aspect of the invention includes the system's own ability of using air pressure to clean the conduits of material post-application. This process can be conducted automatically.

The system can be used in combination with a variety of conveyance methods for the system or the target product to which the substance is to applied, or both.

III. BRIEF DESCRIPTION OF THE DRAWINGS

Figure 2:
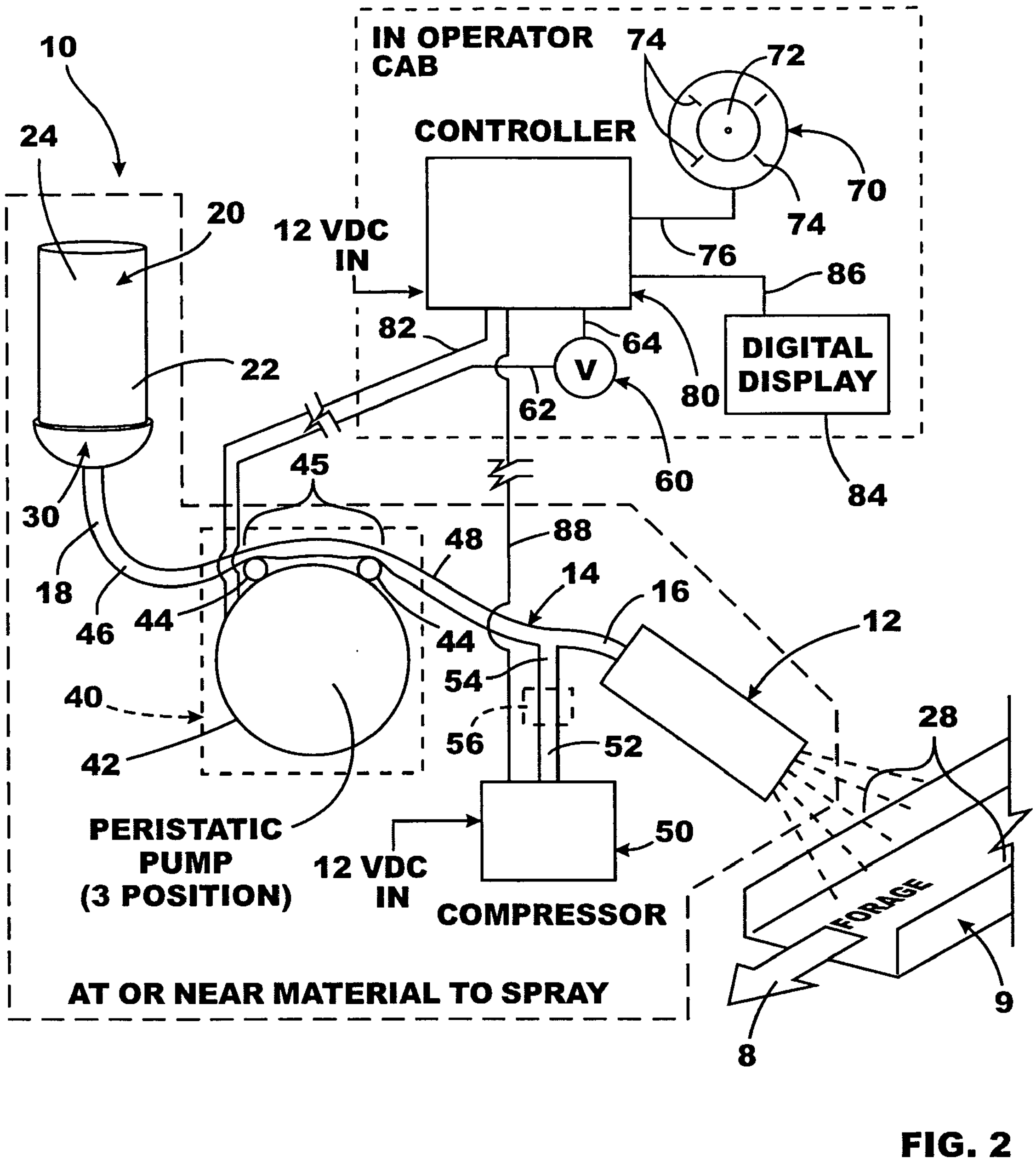
FIG. 2 is a diagram of components of an exemplary embodiment according to the present invention with a single mixture container.
Figure 6A:
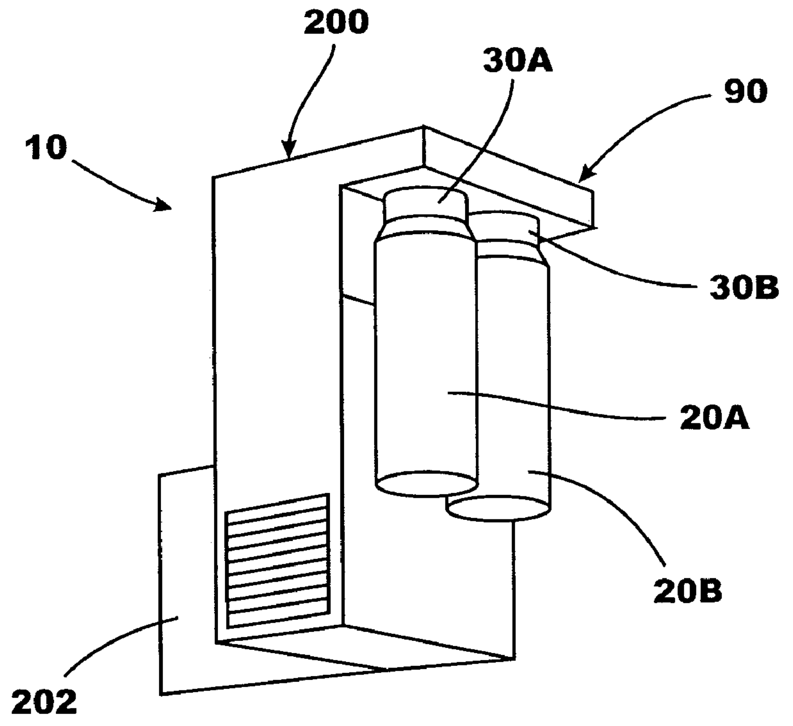
Figure 6B:
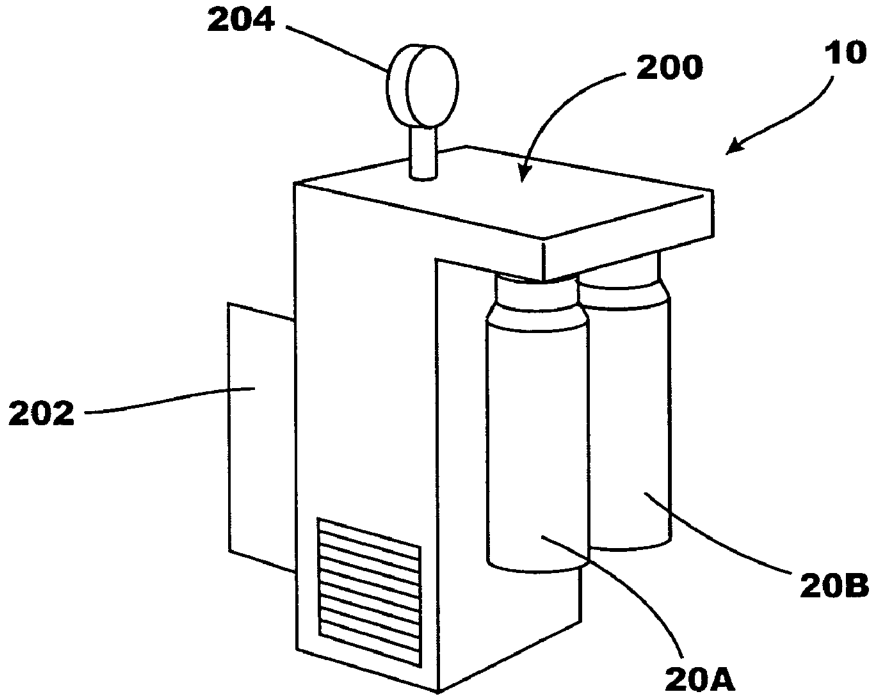
Figure 6C:
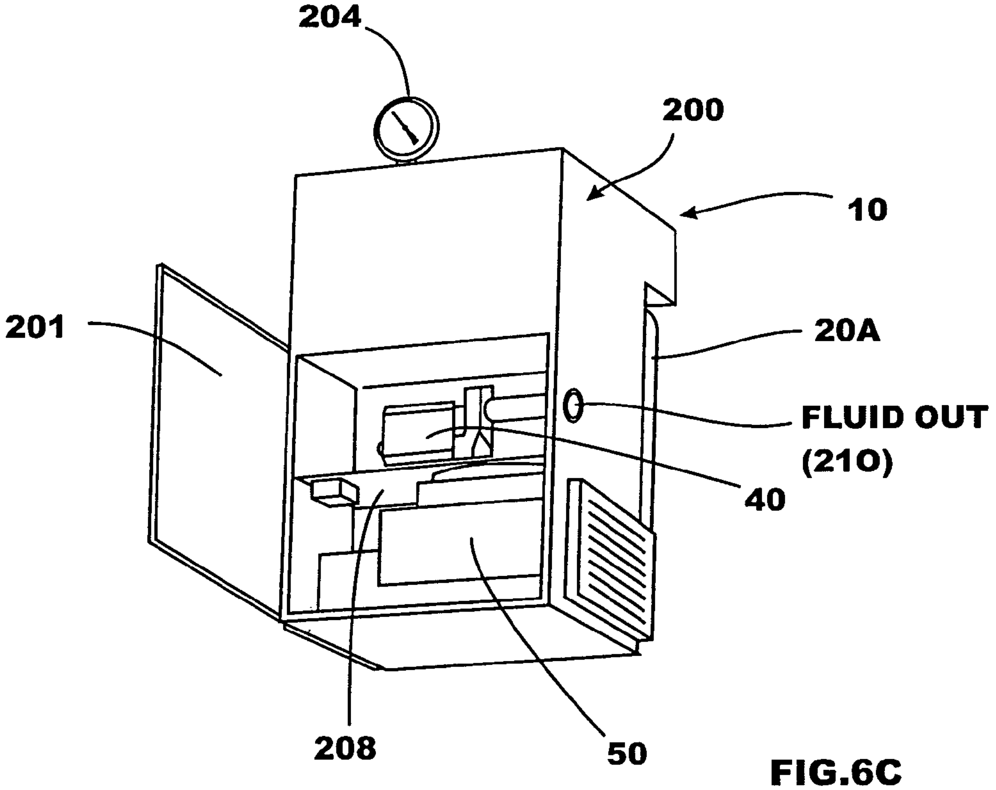

FIGS. 6A–C are perspective views of one example of how certain components of the system of FIG. 2 could be incorporated into an integrated apparatus or housing.

Figure 7:
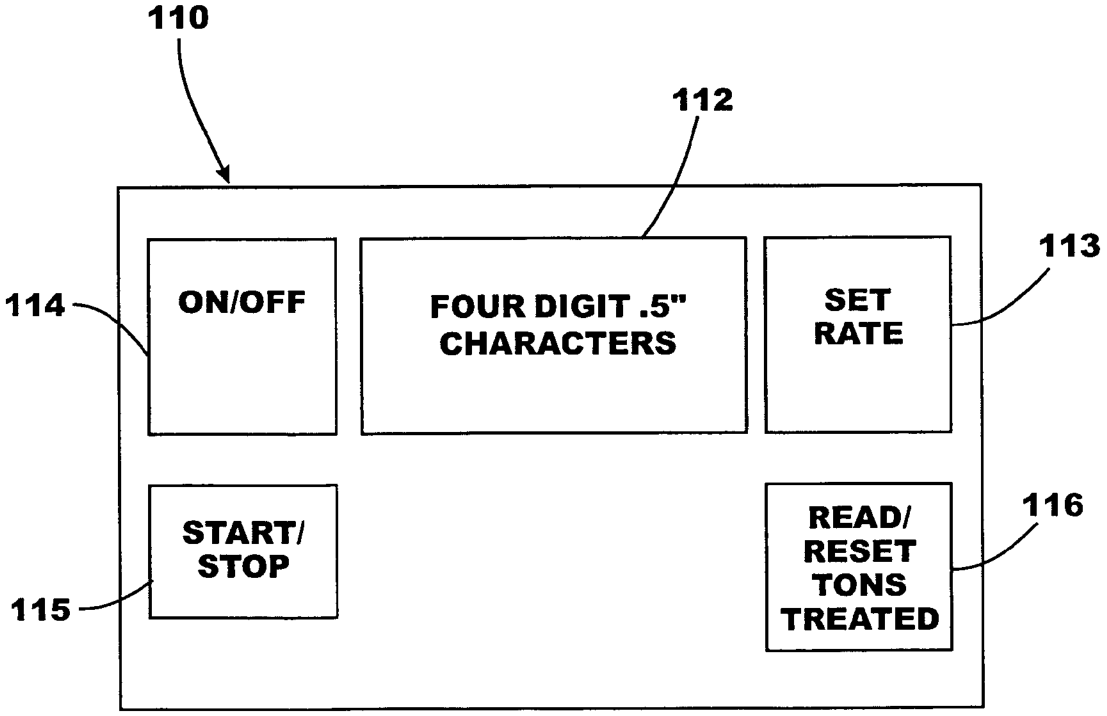

FIG. 7 is a diagrammatic view of a control interface for an embodiment of the invention.

Figure 8:
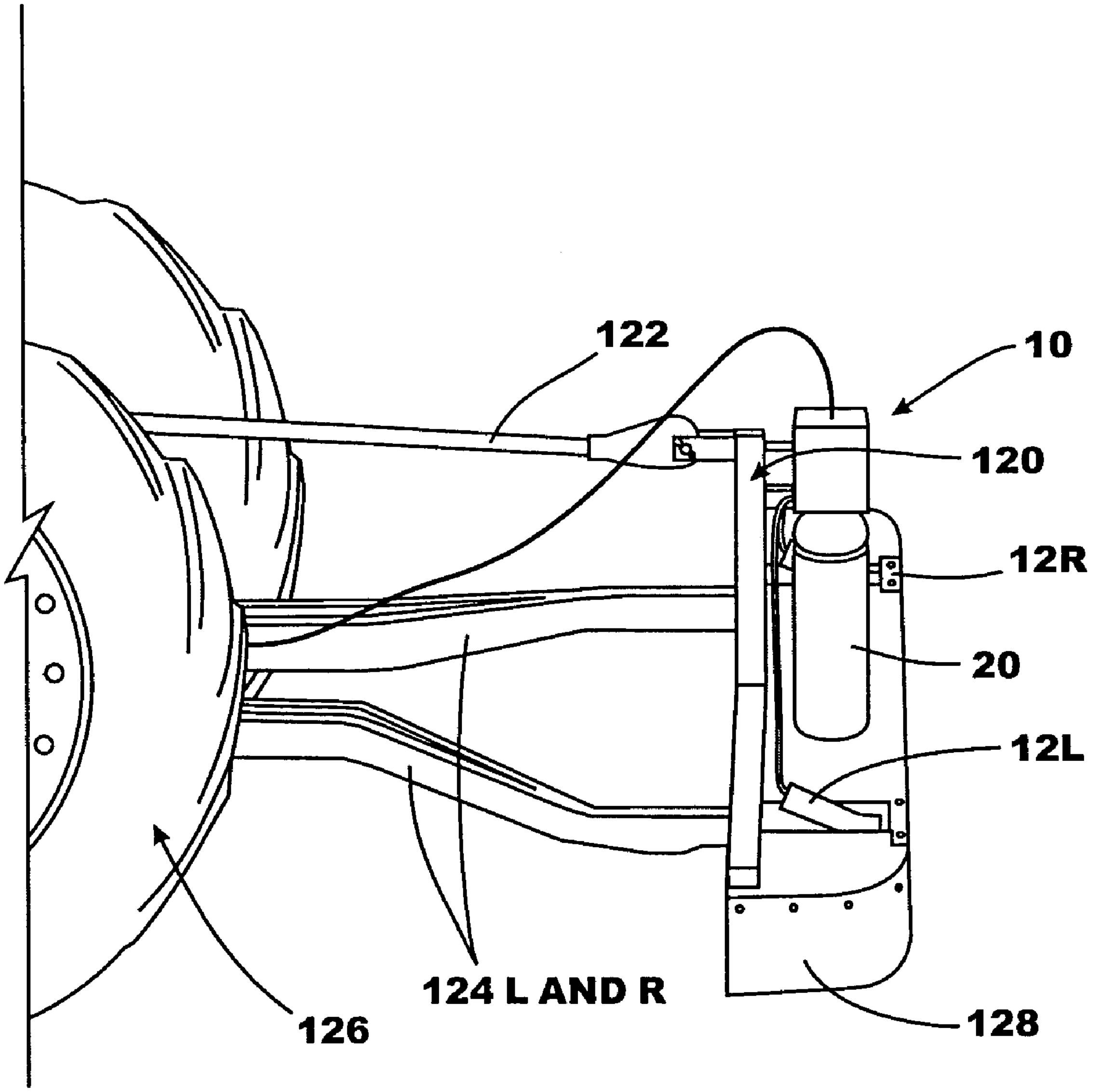

FIG. 8 is a simplified perspective diagram of an alternative embodiment according to the present invention; an embodiment where the biologically active or chemical substance is applied in a swath of mown or cut crop in a field.

IV. DETAILED DESCRIPTION OF EXEMPLARY EMBODIMENTS

A. Overview

For a better understanding of the invention, examples or forms the invention can take will now be described in detail. Frequent reference will be taken to the accompanying drawings. Reference numbers will be used to indicate certain parts and locations in the drawings. The same reference numbers and letters will be used to indicate the same parts and locations throughout the drawings, unless otherwise indicated.

B. Exemplary Embodiment 1

Figure 1:
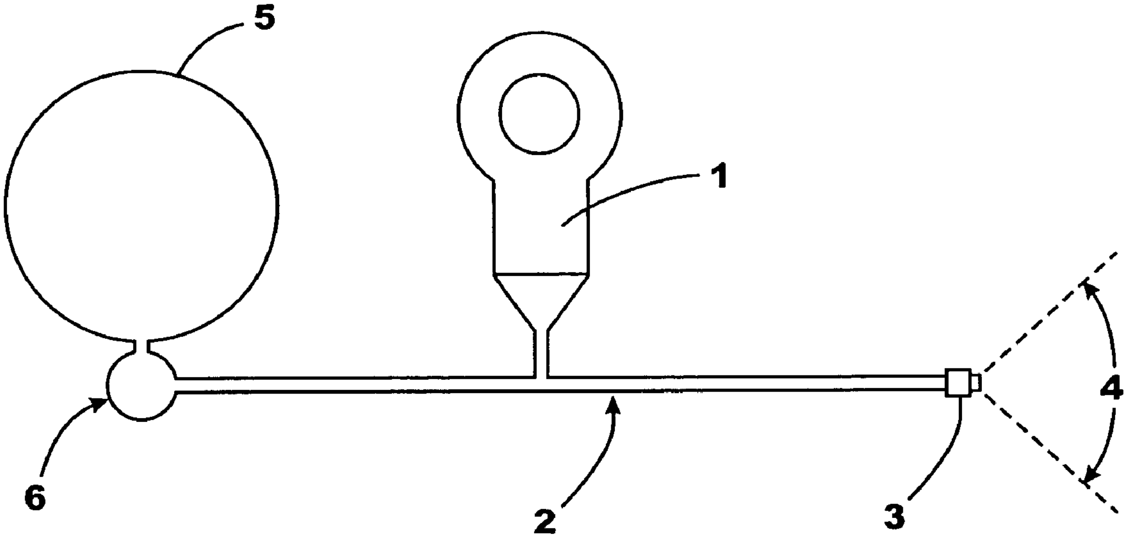
FIG. 1 is a simplified diagram of one exemplary embodiment according to one aspect of the present invention.

With reference to FIG. 1, in one aspect of the invention, an apparatus and process combines a high volume of air delivered to the crop and a low volume metering of the additive (e.g. a mixture of biologically active or chemical substance and water) into the stream of air to carry and distribute the additive into a crop. In a typical embodiment of the process, a means of pumping air 1 is mounted on harvesting equipment such as forage harvesting or baling implements. The airflow from the source 1, a pump, compressor or supply of compressed air, is normally between 0.1 and 5 cubic feet per minute. It is delivered into a line 2 and routed to a spray orifice 3. The orifice will deliver the air in an even fan-type pattern 4 when the air before the tip is delivered under pressure, typically between 5 and 100 pounds per square inch (psi). When this spray orifice 3 is oriented in a position on the harvesting implement where the crop is flowing evenly in front of the tip, the air/liquid mix covers the crop evenly.

In the typical embodiment, a reservoir 5 to hold the additive is also located on the harvesting equipment. A metering device 6 is used to dispense the additive into the line 2. The metering device 6 regulates the proper application of the additive based on flow of the product. The metering device 6 may also have a means of preventing air from flowing into the reservoir 5 and also must have the capability to deliver product into the line 2, overcoming the line pressure developed by the air supply 1. In a typical embodiment, the metering device 6 used is a positive displacement pump, which will prevent air from entering the reservoir 5 and will deliver product at a pressure high enough to overcome the air pressure in the line 2. This pump can be equipped with a means to regulate flow, so that the amount of additive discharged to the crop is matched to the rate of harvest, and the desired ratio of application can be maintained. Distance from the point of introduction at the metering device 6 and the spray tip 3 must be of sufficient length to allow for mixing of the product in the air before it is delivered to the crop.

An encoder could be used to monitor application rate, a voltage adjustable motor to control metering of the concentrate, or other devices to monitor and manage application.

C. Exemplary Embodiment 2

1. Exemplary Environment

With reference to FIGS. 2–7, other aspects according to the invention will be described. In this example, an additive (an air/liquid mix including a biologically active substance mixed with water) will be applied to a harvested agricultural crop, which will be forage such as alfalfa. The biologically active substance will be a forage inoculant (e.g. 1174 silage inoculant, available from Pioneer Hi-Bred International, Inc., Des Moines, Iowa)

The apparatus for carrying and applying the mixture on harvested forage is a self-propelled or pull-behind (including loader wagons) forage crop chopper vehicle or implement (such as are well-known in the art), with the spray nozzle positioned along an internal conveyor or pneumatic movement of the harvested forage. A control device is positioned at or near the operator of the vehicle or implement.

FIG. 2 is a diagrammatic illustration of a system 10 according to this exemplary embodiment. The components are in diagrammatic form for illustration and are not to scale. Forage is diagrammatically illustrated passing through an internal conveyor 9 of the chopper in the direction indicated by the arrow 8 in FIG. 2. Components in the upper right hand part of FIG. 2 are located in a operator cab. The remainder of the system is located at or near the material to spray, internally of the harvester vehicle.

Of course, the apparatus, system, and method can be used for other analogous applications and in other environments, as indicated herein. This is one example only.

The basic primary components of system 10 will now be described.

2. Bottle 20

Figure 3:
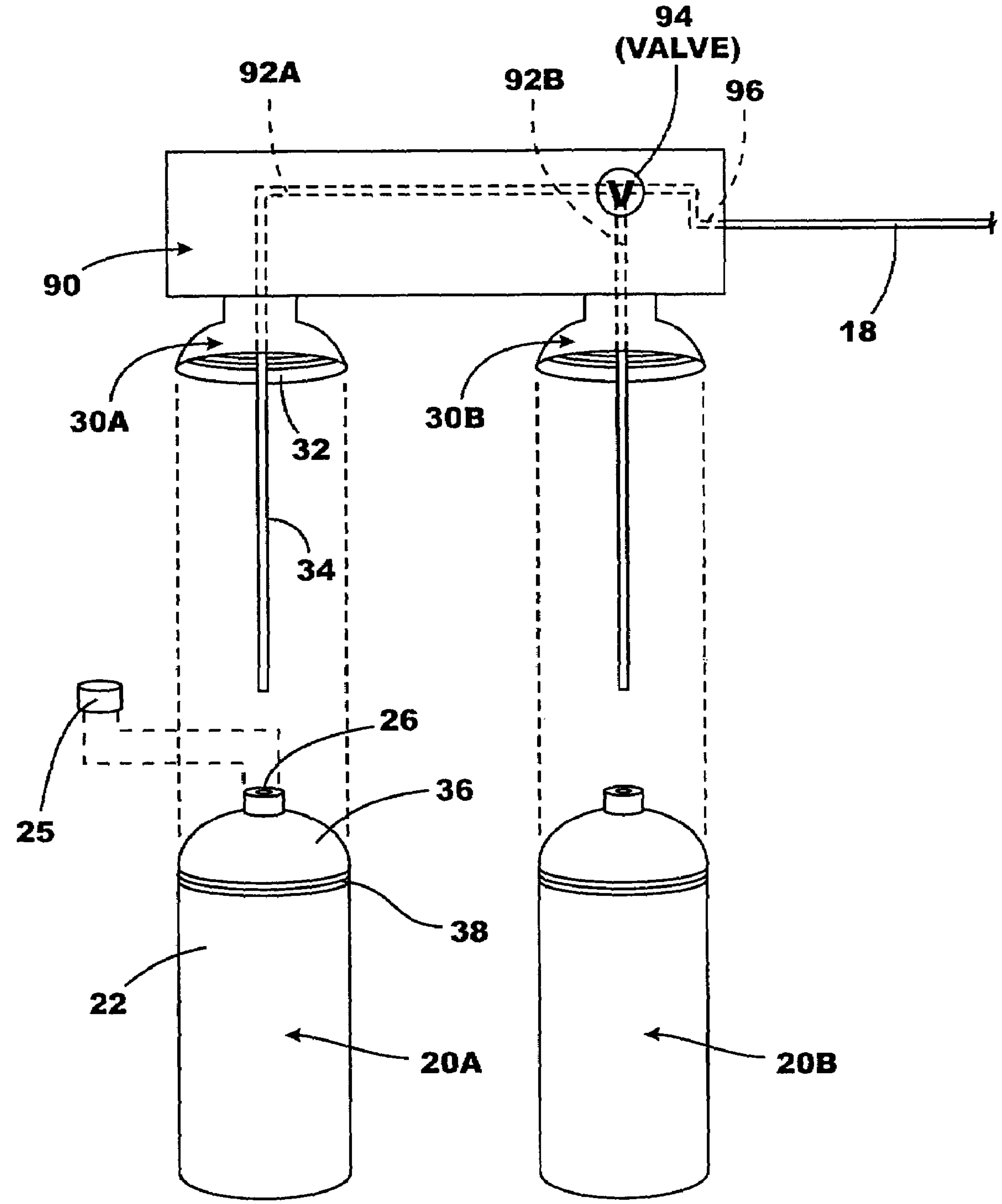
FIG. 3 is a diagrammatic view of a double container system that could be used with the embodiment of FIG. 2.

A 2,500-milliliter bottle 20 (basically cylindrical) with a first end 22 and a second end 24, is adapted to hold a mixture of carrier fluid (e.g. water) and biologically active or chemical substance (e.g. forage inoculant). As can be seen in FIG. 3, bottle 20 can have an opening 26 in end 22 through which the water and inoculant can be inserted into bottle 20 and mixed (by shaking or other methods), or a pre-mix of water/inoculant could be inserted into bottle 20. A removable cap 25 is illustrated in FIG. 3 (e.g. could be placed onto the top of bottle 20 and removably cover and seal opening 26). Bottle 20 could be the Appli-Pro™ bottle from Pioneer Hi-Bred International, Des Moines, Iowa (USA). It could have a configuration like that of U.S. Pat. No. D409,303.

The inoculant is available from a variety of commercial sources in highly concentrated form. Through empirical testing or knowledge, the application amount from system 10 can be determined. The ratio of inoculant to water in bottle 20 can be calculated so that the required ratio of inoculant to volume of forage is met when system 10 is operated.

One example would be to treat about 250 tons of harvested forage per hour. A ratio of approximately 1 part inoculant to 6 parts water for a 2,500-milliliter bottle (e.g. reference number 20 of FIG. 2) would be typical. The 250 tons/hour is based on the assumptions that: (a) system 10 is configured to mist approximately 10 milliliters per ton; and (b) there would be approximately 100 Billion colony forming units (CFU) per ton of forage moving at medium or high speeds through the spraying area.

Bottle 20 can be made of any of a number of materials. One example would be high impact, transparent UV resistant plastic that can be sterilized with traditional procedures.

As can be appreciated, a 2,500-milliliter bottle is easily carryable, even when full, by one or two hands of a person. Several bottles 20 could be carried by a single person at least in a box or carrier. Bottle 20 could include indicia with instructions or identification.

Furthermore, as can be appreciated, a friction fit, sealable cap 25 would allow mixture in bottle 20 to be stored for some reasonable time, as opposed to having to throw it away if not used up in a given application session.

3. Bottle Receiver 30

As shown in FIG. 2, and with further reference to FIG. 3 (left side), system 10 includes a receiver 30 adapted to accept and receive the end 22 of bottle 20 with opening 26. Threads 38 on bottle 20 could mate with threads in concave receiving cup 32 of receiver 30 to allow removable securement of bottle 20 to system 10. Receiver 30 could be operable in the position shown in FIG. 2, with bottle 20 inverted such that fluid would fill by gravity into conduit 14. Alternatively, as indicated in FIG. 3, bottle 20 could be threaded, with opening 26 up, into receiver 30. A tube 34 could extend down near the bottom of bottle 20 when in fully attached position and suction or vacuum effect of pump 40 could draw fluid from bottle 20 up into conduit 14.

Application Ser. No. 10/140,596 and WO 99/58253 illustrate in more detail several embodiments of a receiver/bottle arrangement 20 such that could be used with system 10. In particular note that receiver 30 could be rotatable such that bottle 20 could be threadably inserted with end 26 up so that no spillage occurs, and then the entire receiver/bottle 30/20 combination rotated such that bottle 20 ends up open-end-down to feed its contents by gravity. Or the entire receiver/bottle 30/20 could remain in the fixed upright position. Furthermore, application Ser. No. 10/140,596 illustrates certain ways that flow could be controlled from bottle 20.

Receiver 30 can be made of relatively economical materials such as molded or extruded plastics that are highly durable and resistant to the environment they would experience.

4. Conduit 14 and Nozzle 12

As illustrated in FIG. 2, main fluid conduit 14 has a distal end 16 attached to a nozzle 12, and a proximal end 18 in fluid communication with bottle 20 through receiver 30. System 10 is operable to move mixture from bottle 10 into end 18 of conduit 14, and to end 16 of conduit 14 for spray distribution from nozzle 12. Conduit 14 can be a durable, transparent, flexible plastic tubing (e.g. hospital grade) adapted to work with a peristaltic pump. It can vary in length and dimensions according to need. In one example, it is a 8 feet long, ¼ inchI.D., ⅜ inch O.D. flexible tube made from one of various plastics types or PVC and is available commercially from Grainger Co. of Davenport, Iowa under product number/name 4HL94.

Nozzle 12 can be different styles or configurations. Preferably, it produces a gentle, consistent mist under the pressure and input conditions of system 10. It does not create atomization through micro screens or sharp corners and constrictions in a manner that could provide damaging trauma on a substantial scale to the cells of the inoculant, or provide shearing action to the cells that would tend to damage them. It promotes even distribution into the space through which forage 8 is moving (see reference no. 28 in FIG. 2). In many present-day forage implements, forage 8 moves relatively quickly past nozzle 12 (e.g. sometimes well over one hundred miles an hour). Many implements use pneumatic power to move forage 8, so it is basically fluidized in pressurized air. It therefore is not lying flat, but is moving fast through all parts of a cross-section of the pneumatic conduit. This presents a challenge for even application to forage 8. Some implements use mechanical conveyors. Forage 8 would then be more in a form that is lying on the conveyor. This also presents a challenge to even application.

An example of nozzle 12 would be a spray nozzle sold under the trademark ConeJet available commercially from Tee-Jet Co. and Spraying Systems Co. of Wheaton, Ill. One such nozzle that has been used is marked "ConeJet 10X". Other types are, of course, possible. Preferably, they do not present substantial trauma to the cells of biologically active substances.

5. Pump 40

Pump 40 is a peristaltic pump having a motor 42 and a peristaltic roller mechanism 44, such as are well known and available commercially. An example would be part no. 2P305 peristaltic pump from Grainger Co. of Davenport, Iowa (12 VDC). It is electrically powered and motor 42 could have a variable speed motor control to the motor speed of motor 42, and thus the pumping rate of pump 50.

Conduit 14 would be in fluid communication with bottle 20 and nozzle 12. It could be a single plastic tube passing through peristaltic pump 40, or could have one piece operatively connected between bottle 20 and an input 46 to a piece inside pump 40, and another piece between output 48 of pump 40 to nozzle 12. Obviously, conduit 14 and any connectors, whether conduit 14 is a unitary member or in segments or pieces, are fluid tight from bottle 20 through nozzle 12.

Operation of peristaltic pump 40 in a normal pumping mode would successively constrict a portion of flexible conduit 14 at area 45 (generally between pump rollers 44) to create a pumping action in conduit 14. Motor 42 would be adjustable to vary the speed of the peristaltic rollers 44, which would be in proportion to the amount of fluid that would be pumped through conduit 14.

Adjustment of pumping rate can be calibrated for the substance and target product. Many harvesting implements have sensors which can estimate the amount of tons of crop being harvested per hour. The amount of mixture to be applied per ton harvested crop per hour can be predetermined. The pumping rate of pump 40 can be calibrated for a range of application rates per ton harvested crop per hour. An operator of the harvesting equipment can check the estimated tons/hour the harvester will be processing and then simply punch in or dial in a correlated setting for system 10. If the rate needs to be changed because of a change in tons/hour being harvested, or for a difference crop or target product, a variable speed pump allows the same.

6. Compressor 50

Pressurized air is introduced into conduit 14 between pump 40 and nozzle 12 through conduit 52 from compressor

50 to junction 54 with conduit 14. Conduit 52 can be of the same or similar material as conduit 14. A fluid-tight "T" joint or other connection can be made at junction 54. Alternatively, conduit 14 could be originally manufactured to have branches 16 and 52.

Compressor 50 can be part number 5Z349 available from Grainger Co. of Davenport, Iowa. Preferably, it produces 5–30 psi at 12 VDC. A range of 5–50 psi has been found acceptable, but a range of 5–100 psi can be used. Preferably, branch 52 is protected by a one-way valve or otherwise has an apparatus that prevents the mixture from traveling into branch 52 or into compressor 50.

The psi from compressor 50 can be adjustable and compressor 50 can be operated on 12 VDC. Alternatively, or in addition, another component could be added to the system that would allow adjustment of air pressure from compressor 50 (e.g. some type of pressure control device at or after the outlet from compressor 50).

7. Voltmeter 60

A conventional voltmeter 60 (one such is part no. IT-855 from Grainger Co.) can be in electrical communication by cable 62 with motor 42 of pump 40. By empirical testing and calibration, the amount of throughput of mixture from bottle 20 to nozzle 12 can be correlated with the voltage reading of motor 42. Alternative voltage sensors, e.g. a digital voltmeter, may be used as well.

Cable 64 can communicate the voltage reading of voltmeter 62 to a controller 80 (see FIG. 2).

As mentioned previously, motor 42 would present voltage readings that can be correlated with a varying amount of throughput of fluid through conduit 14. Therefore, by the simple method of monitoring voltage of motor 42, intelligence can be gathered about the rate of mist from nozzle 12.

There can be alternative ways to calibrate the system and operation of motor 42 without voltmeter 60 and its function.

8. Manual Control 70 and/or Control Interface 110

Because mist output has a known relationship to operating voltage of pump 42, manual control 70 can be operatively connected to motor 42. A manually adjustable control knob 72 can be adjusted to different settings 74 for control 70 to provide a range of pump speeds (i.e. motor speeds), to in turn adjust rate of pumping action from pump 40.

One alternative would have control 70 (e.g. a rheostat) directly adjust speed of motor 42. The operator would have to set control 70 based on empirical tests or calibration.

Another alternative, as shown in FIG. 2, has control 70 operatively connected to an intermediary component, here controller 80, which would translate the setting of control 70 into a signal that would instruct the speed of motor 42 through a cable, electrical wire, or other communication channel 82. A cable, electrical wire, or other communication channel 76 can connect control 70 to electronic controller device 80.

Another option would be to have a control interface associated with controller 80 (see, e.g., control interface 110 of FIG. 7) which would allow an operator to set application rate by pushing or touching buttons or screens or other input devices. Software could be programmed to interpret the operator input and instruct pump motor 42 accordingly.

9. Controller 80

System 10 can be coordinated through a controller 80. Controller 80 can be a microprocessor, such as are well-known and commercially available. Other types of electric, electronic, or digital controllers are possible. It could include a digital display 84 integrated with controller 80 or connected through a cable 86. Controller 80 can operate on 12 VDC. As mentioned, adjustable inputs directly on digital controller 80 may be used in place of a rheostat 70.

Controller 80, along with manual control 70 if used, can be integrated into a housing that can be positioned in the operator cab of the agricultural equipment (e.g. chopper). Voltmeter 60, if used, can be integrated into the housing or positioned near pump 40, or anywhere in between.

Controller 80 could be programmed by well-known means and methods to interpret and instruct pump motor 42 to operate at a selected setting of control 70 and monitor voltage of motor 42 to maintain a consistent pump motor 42 speed. An example of operation is provided later.

Alternatively, controller 80 could be programmed for more sophisticated functions. For example, it could have either a volatile or non-volatile memory with look-up tables correlated to various application rates. Instead of a manual control 70, the operator would simply enter an input instruction that controller 80 would interpret to be a given application rate. Controller 80 would then, in turn, instruct operation of pump 42 accordingly. Voltmeter 60 could effectively be a feedback loop to controller 80 to monitor the pump operation and thus allow controller 80 to fine tune the mist output.

Memory could also contain application rates and ranges for a variety of different biologically active or chemical substances.

Optionally, controller 80 and other electrical or electronic circuitry or components could be manufactured, in whole or in part, into a circuit board that could be installed in a housing for operable use with apparatus 10. This could further reduce cost of the system.

10. Electrical Circuit

Figure 5:
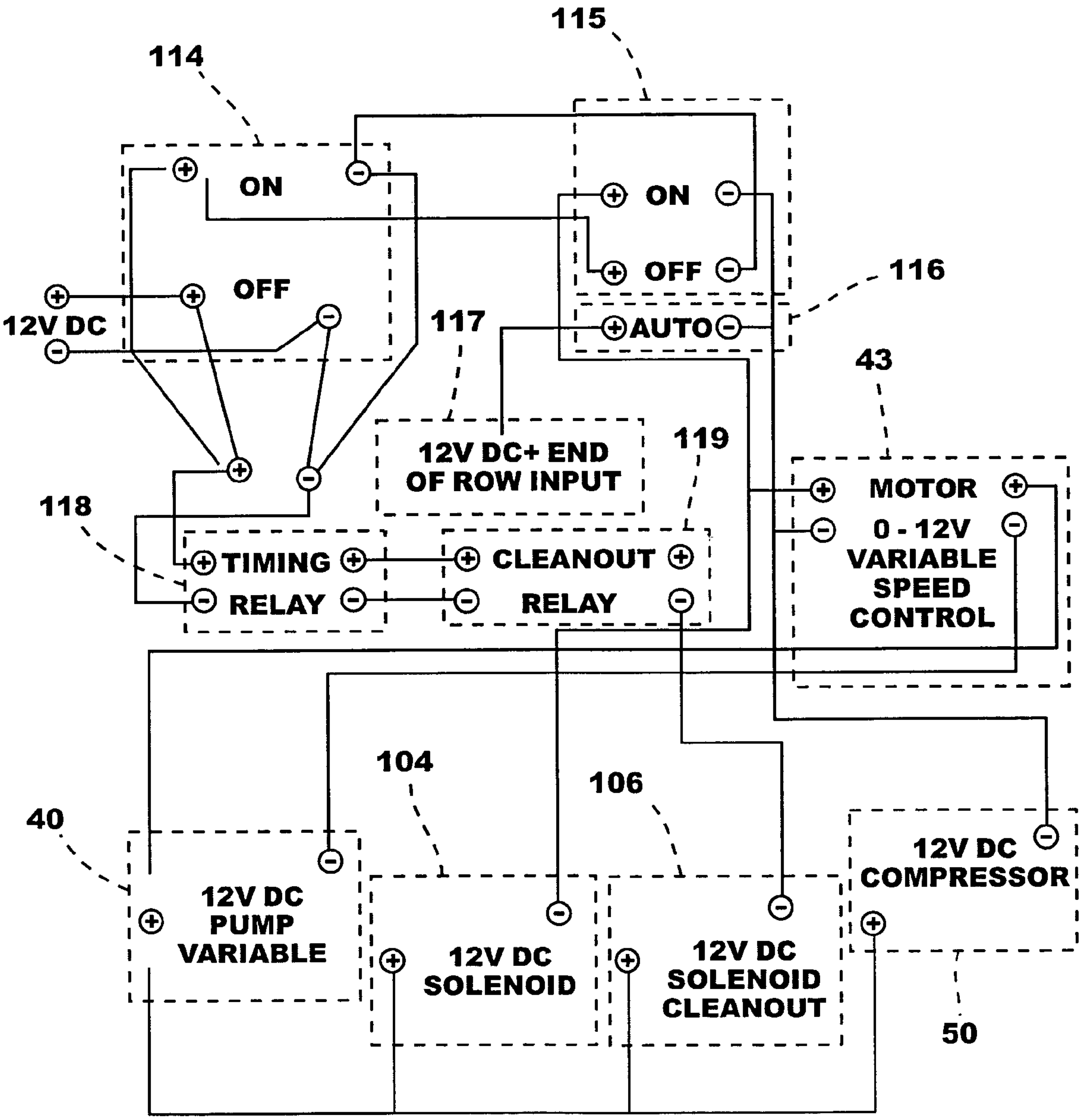
FIG. 5 is an electrical schematic of an electrical circuit usable with the embodiment of FIG. 2.

FIG. 5 schematically illustrates generally an electrical circuit 100 that can be used with system 10. Circuit 100 electrically communicates between the components of FIG. 2 and a 12 VDC electrical power source.

For example, FIG. 5 illustrates the following components. It could include additional components.

A switch 114 can provide electrical power to the circuit. A switch 115 can turn the spraying mode on. An input 117 can automatically pause the spraying mode by disconnecting power to pump 40 and compressor 50 when a signal is received at input 117. Input 117 here is an "end of row input", which can be a signal from a micro-switch or other component on the harvesting implement indicating the harvesting head of the implement has been raised. This, in turn, indicates that harvesting has stopped. Conversely, the circuit can automatically resume spraying mode when the harvesting head drops, which can be sensed and signaled to circuit 100.

A variable speed control 43 for pump motor 42 of pump 40 can be set to control rate of pumping action of pump 40.

FIG. 5 also illustrates two valve control solenoids 104 and 106 which could be used to turn valves (not shown) on and off by instruction from controller 80. Details of their operation are provided later. Solenoids 104 and 106 can be used to open and close pathways for pressurized air and fluid on conduit 14. Solenoid 104 can be normally closed to block and seal conduit 52 to compressor 50 when it is not operating. Solenoid 106 can operate in concert with solenoid 104 for an optional clean out mode for system 10, as will be discussed later. A timing relay 118 can be used to control a cleanout relay 119, which in turn can control actuation of cleanout solenoid 106. Timing relay 118 essentially can operate for a fixed period of time (e.g. 30 seconds) to run an automatic cleanout mode if instructed by controller 80.

11. Integrated System/Housing

FIGS. 6A–C illustrate one way some of the components of device 10 can be integrated into a relatively small housing 200 (e.g., sheet metal) that can be installed on a vehicle or wherever else could be useful. A mounting plate 202 provides a surface that can be bolted or otherwise mounted on vehicle or wall or other surface. A header 90 could include a receiver 30 for one or more bottles 20. In FIGS. 6A–C, two APPLI-PRO™ bottles 20A and B can be screwed into operative position to receivers 30A and B respectively. This provides easy access for the operator to connect or remove either bottle 20A or B to device 10. As indicated at FIG. 6C, a door 201 in housing 200 allows access to pump 40, compressor 50, and other components (e.g. solenoids, valves, tubing), . A wall 208 can separate and essentially seal off compressor 50 from pump 40.. A circuit board could contain much of the circuitry indicated at FIG. 5, but would usually be mounted in an enclosure in the operator cabElectrical connections would communicate operating instructions to pump 40 and compressor 50 in housing 200. Conduit 14 and conduit 52 are not shown specifically in FIG. 6C, but would form fluid pathways from bottles 20A and B and compressor 50, respectively, to a fluid outlet 210 from housing 200. The branch of conduit 14 to nozzle 12 (not shown in FIG. 6C) would operatively connect to fluid outlet 210.

As indicated in FIG. 2, controller 80 and other components could be located remotely from housing 200 (e.g. in the operator cab of the vehicle). Conventional electrical communications (wire or wireless) could communicate instructions or information from the in-cab components to housing 200 to, in turn, instruct operation of solenoids 104 and 106, pump 40 and compressor 50.

FIGS. 6B and C show an optional pressure gauge 204 could be operatively connected to conduit 14 to monitor pressure during operation of system 10. It should be noted it could be placed in any of a variety of positions. It could communicate with controller 80 to provide real-time information to the operator in the cab. As an alternative, a digital readout on the controller could also give a pressure indication.

As can be seen in FIGS. 6A–C, most of system 10 can be integrated into a relatively compact single housing 200 that would be relatively easy to mount, even in sometimes cramped interior spaces of a vehicle or implement. With relatively few connections, housing 200 can be in communication with controller 80 and nozzle 12. This provides easy and non-cumbersome installation, set-up, and maintenance. It also allows removal of system 10 and installation into another vehicle or place with substantial ease.

As can be appreciated, the components of system 10 could be predominantly modular in nature, and thus present efficiencies in manufacturing, maintenance, repair, and replacement.

D. Operation

In operation, system 10 can function as follows. There would be preliminary steps such as below.

Bottle 20 would be filled with a mixture of water and inoculant according to a priori knowledge or recommended instructions for a given application rate, crop and/or inoculant. The operator could, by hand, uncap bottle 20, and connect it to receiver 30.

Prior testing is used to program controller 80 such that manual selector 70, or in this example, user control interface 110, would provide the operator with the ability to enter any of a range of application rates programmed into controller 80.

Nozzle 12 would be pre-positioned adjacent the flow path of forage 8. Of course, the spray pattern of nozzle 12 can be tested, its spray pattern established, and the position of nozzle 12 adjusted to get desired coverage relative moving forage 8 (FIG. 2) without wastage or over-spraying.

Some design is needed as far as placement of the components internally of the vehicle. In one embodiment, bottle 20, receiver 30, pump 40, compressor 50, and the majority of conduit 14 could be enclosed within a housing or framework like housing 200 of FIGS. 6A–C and inserted near the desired position of nozzle 12 in a location that will not come into conflict with other operating components of the vehicle. Alternatively, any or all of the components can be mounted in desirable positions and operably interconnected.

By referring to the electrical schematic of FIG. 5, electrical power to various components could be obtained by a connection to the vehicle's battery power system (usually 12 VDC) or otherwise converted to 12 VDC so that system 10 does not need a power source external of the vehicle.

The advantages of system 10 would therefore include a relatively small-sized, interchangeable, removable bottle 20 that could be handled by hand, in combination with a fluid pump and air compressor to provide an aerated fluid flow to produce a mist of even consistency and application; all without having to use an atomization or atomizer structure or method, which can be expensive and could be detrimental to biological cells or life forms.

Controller 80, or some other intelligent device, can be used to not only instruct operation of components like pump 40, but also coordinate operation of the system and provide intelligence regarding settings or operation for the various components for a given mixture, crop, and throughput of crop. For example, sensors like a voltmeter, pressure gauge, or others could send information to controller 80 which could be used by its programming to control system 10.

The general rules for operation are as follows:

a. Eliminating atomization to reduce shearing action or trauma that could damage bioactive or chemical substances.
b. Maintaining a closed system between the mixture in bottle 20 and nozzle 12 deters any drying action that could be detrimental to biologically active or chemical substances.
c. Elimination of an atomizer or certain types of pump, and introduction of pressurized air, deters high temperatures for the mixture, which also could be detrimental to a biologically active or chemical substance.
d. Rate and consistency of spray can be relatively precisely controlled by operation of pump motor 42 and amount of pressurized air 50.
e. Size, weight, and cost of system 10 are relatively small compared to existing typical systems. Elimination of a large multi-gallon tank eliminates a lot of weight and size issues. Additionally, elimination of a hundred gallon tank or water container eliminates a safety issue because such a tank adds a significant amount of weight to a vehicle and could create tipping problems.
f. The rather compact size of the system allows it to be placed advantageously relative to the crop to be sprayed, including internally of vehicles. This can eliminate the need for applying the substance to the crop in external positions of the vehicle, which then brings into play environmental factors such as wind that could affect the mist. Additionally, utilizing the pressurized air from compressor 50 allows the system to be placed in environments that pull a vacuum. The mist will still work effectively.

One specific description of components and operation according to one exemplary embodiment is as follows. The controller 80 can output motor functions to a peristaltic pump 40, air compressor 50, and solenoid valves in an application system for crop inoculant, such as has been previously described.

A. Physical specifications:

1. Peristaltic pump 40: 12 volt DC gear motor 42 runs between 300 and 1800 rpm and draws a maximum of 3 amps. The pump will be located 8 feet away from the controller 80. The distance of the pump from the controller 80 may vary in distance. The controller80 will regulate motor speed to control output.
2. Compressor 50: The controller80 will turn the compressor on and off only. 12-volt power at 15 amps will be supplied to the compressor externally. Optionally, a pressure control device or PCD (available commercially—see component 56 in dashed lines in FIG. 2) could be used to adjust the amount of air pressure from compressor 50 to conduit 14. PCD 56 could be controlled by controller 80 if desired, through a solenoid or other electronically-controlled device. Alternatively, it could be manually operated or perhaps even by automatic adjustment via sensors.
3. Solenoid valves: There will be two solenoid valves to control the direction of airflow. Control to these valves will be to energize a 12-volt coil of valve control solenoids 104 or 106, opening up a normally closed valve that will require 0.2 amps to maintain the open position for an interval (e.g. 30 sec.). Power to the solenoids 104 and 106 will be activated by the controller 80 for an interval of 30 seconds.
4. Display of control user interface (see FIG. 7): The controller 80 will have a display 112 that shows motor speed setting and the accumulated revolutions of the motor based on a calculation of motor speed and duration of operation. These values will be displayed as a function of harvesting units, which is derived by simple math from the motor speed setting. A one line 4-character display with LCD numbers at 0.5-inch character height could be used, or other styles and configurations of display. If possible without significant cost, the display will also include a reading to give an indication of line pressure. The purpose of this pressure display is to provide the operator with a warning of possible plugging. Therefore absolute accuracy in pressure reading is not required.
5. Enclosure 200: The unit will be installed in tractor cabs requiring dust and moisture resistance similar to a Harvest Tec 477 acre meter (available from Harvest Tec, Hudson, Wis.). The vibration requirement for the controller 80 should be good enough to provide years of dependable service without vibration induced breakdowns. Consideration should be made for conditions under which the unit will be operated.
6. Power supply: The controller 80 will be powered off the tractor's 12-volt power system that will deliver between 11 and 15 volts of DC power.
7. Cabling: Power input will be plugged into the bottom of the box. Motor output and compressor output will be plugged into the bottom of the box. Amp connectors will be used on both connections. Connections between the pump housing and the control box should be some type of couplers, screw on, or quick disconnect which will enable the operator to interchange units easily and fairly quickly.
8. Switches: A membrane face overlay with four membrane switches 113, 114, 115, and 116 (see FIG. 7) will be over-laid on the box face.
9. Start/stop: Operation will be controlled by either a box-mounted switch 115 or from a remote signal that activates with 12-volt positive input.

B. Control Operation (refer to FIGS. 2, 5, and 7):

1. Power up and start non-operating part of "on" cycle. A push of "on/off" button 114 is essentially the "power" button for system 10 and enables the supply of electrical power to controller 80. This initiates a what will be called the non-operating part of an "on" mode or cycle, where the display becomes lighted and the "set rate" and "read/reset tons" functions (correlated with buttons 113 and 116 on control interface 110) are enabled.
2. Clean functions. There are times when it is desirable to clean up conduit 14 and nozzle 12. In this embodiment, when power button 114 is pushed off, controller 80 will automatically initiate an automatic clean mode or cycle. It does this by activating the two solenoids 104/106 and the compressor 50 for a pre-determined, pre-set interval (e.g. 30 seconds). The solenoids set valves in the fluid paths between compressor 50, nozzle 12, and bottle 20 so that the following can occur. Pressurized air from compressor 50 is allowed to travel to nozzle 12. This will remove any fluid from that part of the fluid pathway and clean out nozzle 12. Controller 80 would also instruct pump 40 to operate, but in a reverse flow mode. This would move any fluid in line 14 back towards or into bottle 20. If the power is re-activated during the 30-second automatic clean period, the 30-second interval will be completed before normal operation is resumed. During the 30-second interval, display 112 will flash "clean". Also, anytime during the "on" cycle, if on/off button 114 is pushed and held for 3 seconds, controller 80 will activate a manual clean mode or cycle. Controller 80 will supply power to solenoids 104/106 as described immediately above and run the compressor 50 until on/off button 114 is pushed again. Display 112 will flash, "clean" during this mode. This allows the operator to run a clean out by manual selection. As can be appreciated, controller 80 could be programmed to automatically run a clean mode at any time.
3. Set rate function. After power up and enablement of it, the "Set Rate" function will be activated in what will be called the non-operating "on" mode, meaning the spraying function of system 10 is not allowed. The operator can then set a desired application rate for the mixture. Pushing "set rate" button 113 will show the rate set on display 112. Holding "set rate" button 113 in will scroll display 112 between the range of values 10 and 400; in 2 unit increments between the sub-range 10 and 100, and in 10 unit increments between the sub-range 100 and 400. When the unit gets to value 400, it will roll over to 10. Scrolling will be at an accelerated rate of 4 to 10 characters per second during the hold down interval. When button 113 is released, the motor speed for pump motor 42 will be set. This speed setting will be accomplished by modulating the ground on the power to the gear motor 42. There can be a look-up table with values of voltage versus pump output. The operator thus selects an application setting via control interface 110 appropriate with a desired rate of application for the given inoculant/water mixture in bottle 20 and the forage speed and volume.

4. Tons treated function. After power up and enablement of the "Tons treated" function, pushing "tons treated" button 116 will cause controller 80 to read the theoretical revolutions of the gear motor for the set "rate value" off of the look-up table. This value will be multiplied by the minutes run and converted to a tons value for display 112. This "tons treated" function can assist the operator, if needed. Resetting the value is accomplished by pushing and holding button 116.
5. Start operating part of "on" cycle. When the vehicle begins harvesting the forage, the operator would turn on the spraying function of system 10 via switch 115. After the non-operating part of the "on" cycle is completed, with the operator having set the application rate, a push of "start/stop" button 115 will begin the operating part of the "on" cycle, where the mixture is sprayed. Controller 80 energizes both pump 40 and compressor 50, and sets solenoids 104 and 106 so their respective valves allow fluid from bottle 20 and pressurized air from compressor 50 to mix and move to and out of nozzle 12. Pump 40 would pull mixture from bottle 20 at the desired rate. Compressor 50 would aerate the mixture at a preset amount. Controller 80 would send a signal via cable 82 to pump motor 42 of pump 40 to operate at a speed proportional to that selected. At the same time, compressor 50 could be instructed by controller 80 to begin operation. The aerated mixture would then be misted out of nozzle 12 as forage 8 passes by the location of nozzle 12 to distribute the selected amount of mixture on forage. In one example, 10 milliliters/ton of forage additive would be applied. In one embodiment, capacity of system 10 is 400 to 600 tons per hour (tph) top end. Typically, 150–300 tph would be treated. During the "run" mode of this operating part of the "on" cycle, display 112 will show the accumulated tons treated. The operator can stop spraying by pushing button 115. During this "stop" state or mode, display 112 will read "stop". The operator will thus have a visual indication of state of spray. A remote signal to 12 volt positive will perform the same function as the "start/stop" key 115. As previously mentioned, the system could be programmed to start or stop automatically if so desired (e.g. by response to dropping of harvesting head).

This air assisted arrangement allows for precise, efficient, economical control of rate and distribution of the mixture with control over temperature, shearing, and drying.

E. Options And Alternatives

The foregoing detailed description is of but one form the invention can take. Variations obvious to one skilled in the art are included in the invention, which is solely described by the claims herein.

For example, variations in each of the components are possible. Dimensions, specifications, and characteristics can vary according to desire and need.

As previously stated, the invention can be used for spraying forage inoculant on harvested forage, but could also be used to apply other types of mixtures that include biologically active or chemical substances on other harvested agricultural crops, or other products or things. Or the invention can be used to apply mixtures before a crop is harvested. For example, it could be applied to a swath of mowed forage before it is picked up and chopped. It could also be used to apply a mixture to a swath or row(s) of growing plants.

Some examples of other substances for application to target product include, but are not limited to, insecticide, herbicide, fertilizer, paint, cleaning fluids, coatings, freeze-drying. Other are possible.

An example of a different use of system 10 from that installed on a harvesting implement is shown in simplified form at FIG. 8. A system 10 (such as shown in FIG. 1 or 2) could be mounted on a frame 120 that has connections to the three arms 122, 124L, and 124R of a three-point hitch of tractor 126. System 10 would include a container 20, a pump 40, a compressor 50 and a controller 80 like previously described. A hood 128 is also mounted on frame 120 with at least one (here there are two) nozzle 12 positioned so that the outlet of the nozzle(s) are inside hood 128. Appropriate wiring and fluid conduits connect the various components in a similar manner as discussed previously. The arrangement of FIG. 8 is configured so that it can be moved by tractor 126 over a swath of mown hay or silage of about three feet wide and apply a mixture from container 20 to the swath in a manner such as has been previously described. Hood 128 helps contain the mixture as it moves out of nozzles 12L and 12R, and helps prevent wind or debris from affecting the application. System 10 can be adjusted up or down relative to the swath by conventional operation of the three-point hitch.

Analogous structure could be used to apply mixtures to cut or growing crops, but not yet harvested ("pre-harvested"). For example, the system 10 could be mounted to the front of a vehicle (e.g. by a frame or connection to the front of a tractor or other implement). It could be operated to apply a substance on crop, whether growing in the field or cut and laying in the field, as the vehicle drives by or over it.

As previously stated, harvesting equipment exist that are self-propelled and direct harvested crop into an on-board bin, a wagon pulled by the harvester, or a wagon pulled along-side the harvester by separate tractor. There are also harvester implements that are pulled behind a tractor and direct harvested crop into a following wagon (either hooked to the implement or moving with the implement). There is also a type of harvester equipment sometimes called a loader wagon, which is pulled behind a tractor but combines a harvester with a wagon. System 10 could be placed in the entrance to the loader wagon or its outlet, and be used to apply substances to silage as it enters the wagon or as it leaves the wagon for placement in a silo or other storage location. The invention can be applied to any of these versions of harvesting equipment.

A system 10 could also be operably positioned and used on other types of vehicles, equipment, or implements.

FIG. 3 shows an optional feature that could be utilized. Two receivers 30 (reference numerals 30A and 30B of FIG. 3) could be mounted in a common manifold 90. Channel 92A would be in fluid communication with receiver 30A and channel 92B with receiver 30B. A valve 94 could select between channels 92 A and B. Manifold outlet 96 could be in fluid communication with end 18 of conduit 14.

With this embodiment of FIG. 3, two bottles 20 could be available for system 10 depending upon position of valve 94. This could provide double the amount of mixture. First bottle 20A could be exhausted, then bottle 20B. Alternatively, different mixtures could be contained, and selected from.

A still further option could be that bottle 20B contain just water. During spraying of a mixture containing a biologically active or chemical substance from bottle 20A, valve 94 would be in a position to block channel 92B to container 20B. At some point, selected by the user, valve 94 could be selected to block channel 92A and pump 42 operated to pull clean water from container 20B to clean out conduit 14 and nozzle 12. Once the system is clean, valve 94 could be turned back to open channel 92A and block channel 92B.

Figure 4:
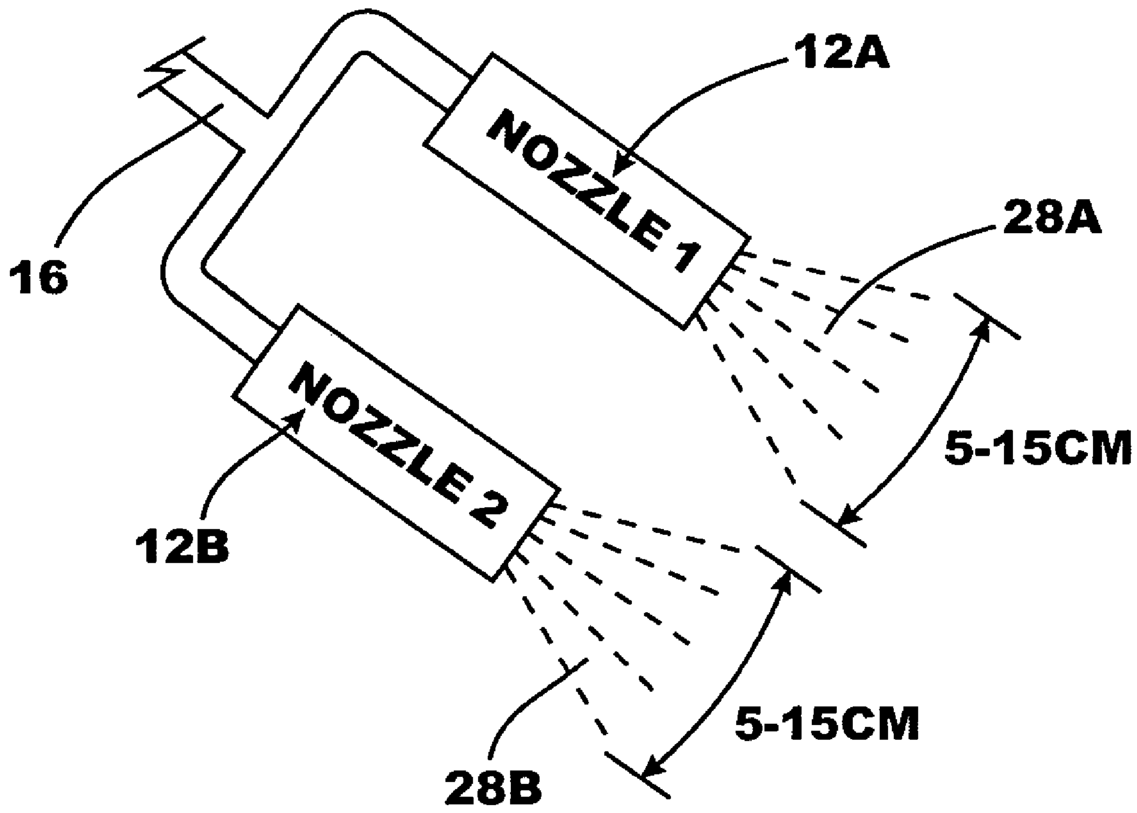
FIG. 4 is an alternative embodiment for a double nozzle system useable with the system of FIG. 2.

FIG. 4 shows another optional alternative embodiment. End 16 of conduit 14 could be in fluid communication with a plurality of nozzles 12. As shown in FIG. 4 for illustration purposes only, two nozzles 12A and 12B are shown in parallel from end 16 of conduit 14. They both could be directed towards harvested agricultural crop coming through the same conveyor. Alternatively, they could be directed to different streams of agricultural crop in two conveyors. As indicated in FIG. 4, a typical width of mist might be 5 to 15 centimeters wide at the harvested crop. However, variations in width and mist patterns are possible.

As can be appreciated, the system could have one, or more, nozzles 12 depending on design and need. Still further alternatively, a system 10 could have multiple bottles 20, each with its own pump 40 and compressor 50 and nozzle 12, to concurrently have a plurality of systems 10 operating. They could be under the operation of one controller 80.

FIG. 5 illustrates an exemplary electrical schematic such as might be used with system 10 of FIG. 2. Alternatives are possible. For example, the circuit of FIG. 5 could be implemented into a circuit board or printed circuit board. In mass production, this could materially reduce cost of the overall system 10.

An additional option could be a sensor indicating when bottle 20 is near or at empty. It could be some sort of optical detector, pressure detector, or some sort of float in bottle 20. Such alarms are available commercially.

Manual control 70 could have a plurality of settings 74 correlated to different "tons per hour" application rates. Control 70 could be a click dial with indicia placed at settings 74 so that the operator could read the "tons per hour" settings and turn the dial by click stop to a desired setting. There could be a digital voltage readout.

Other additional features are possible.

As previously indicated, instead of system 10 being stationary relative to moving agricultural crop, system 10 could be moved past stationary agricultural crop. Alternatively, spraying system 10 could be in movement as the agricultural crop is also moving.

Examples of different environments, applications, and configurations are set forth in Ser. No. 10/140,596. Other examples are possible.

A different container or bottle from bottle 20 could be used.

It can be seen that the invention meets at least all its stated objectives. It provides for controlled rate and distribution with control of temperature, shearing, and drying. Typically a +/−5% application rate variance or tolerance is acceptable. Utilizing components of the type described above, system 10 could be made to cost under $1000, and likely well-under that amount. This is significantly less than the atomizing systems discussed earlier. It allows high capacity (e.g. hundreds of tons per hour), precise control of small amounts of bioactive or chemical substances, but with even, controlled rate and distribution.

What is claimed is:

1. An apparatus for applying a relatively small volume of biologically active or chemical substance to a relatively large volume of crop comprising:

(a) a fluid container adapted for containing a mixture of water and biologically active or chemical substance, including an opening for filling and removal of fluid;

(b) a nozzle with a spray orifice;

(c) a conduit adapted for fluid communication between the fluid container and the nozzle;

(d) a source of pressurized air in fluid communication with the conduit between the fluid container and the nozzle;

(e) a pump operatively positioned relative the fluid conduit and adapted to move the mixture from the fluid container to the conduit;

(f) a releasable connection in fluid communication between the conduit and the container, the releasable connection comprising a receiver which can retain, in a releasable fashion, the container;

so that mixture pulled from the fluid container by the pump is aerated from the source of pressurized air and delivered out of the spray orifice of the nozzle.

2. The apparatus of claim 1 further comprising:

(a) a voltage sensor operatively connected to the pump to sense operating voltage of the pump;

(b) a user input having a plurality of settings correlated to different application rates;

(c) a controller having inputs operatively connected to the voltage sensor and user input and an output operatively connected to the pump so that operating voltage of the pump is correlated to the user input setting, which is proportional to the application rate.

3. The apparatus of claim 2 wherein the user input comprises a rheostat or similar device.

4. The apparatus of claim 2 wherein the controller comprises a microprocessor.

5. The apparatus of claim 2 wherein the controller includes a user display.

6. The apparatus of claim 1 wherein the crop is one of forage, grain, hay, and feed.

7. The apparatus of claim 1 wherein the crop is harvested crop.

8. The apparatus of claim 1 wherein the crop is crop cut and lying in field in a swath.

9. The apparatus of claim 1 wherein the crop is growing crop.

10. The apparatus of claim 1 wherein the biologically active or chemical substance comprises at least in part, living organisms.

11. The apparatus of claim 10 wherein the living organisms comprise bacteria.

12. The apparatus of claim 11 wherein the bacteria is adapted to be effective as a forage inoculant.

13. The apparatus of claim 1 wherein the fluid container is a size which is hand carryable.

14. The apparatus of claim 13 wherein the fluid container size is in the range of a fraction of a liter to several liters in volume.

15. The apparatus of claim 1 wherein the fluid container is sealable and removable from the apparatus.

16. The apparatus of claim 1 wherein the releasable connection is translatable to allow connection of the container in at least either upright and inverted positions.

17. The apparatus of claim 1 wherein the nozzle provides substantially uniform consistent spray but not atomization of the mixture.

18. The apparatus of claim 1 wherein the conduit is somewhat flexible and fluid impermeable, with open opposite ends.

19. The apparatus of claim 18 wherein the conduit is made of plastic.

20. The apparatus of claim 1 wherein the pump comprises a motor which is voltage-controlled and adjustable.

21. The apparatus of claim 20 wherein the pump is a peristaltic pump.

22. The apparatus of claim 1 wherein the source of pressurized air comprises a compressor producing pressurized air output on the order of 5 to 100 psi.

23. The apparatus of claim 1 wherein the mixture comprises relatively small amounts of biologically active or chemical substance metered into a relatively high volume of pressurized air.

24. The apparatus of claim 1 wherein the pressurized air from the source of pressurized air and rate of pumping action of the pump are coordinated to produce misting action at the nozzle.

25. The apparatus of claim 1 further comprising a power source which produces DC voltage.

26. The apparatus of claim 25 wherein the DC power supply comprises an agricultural type electrical system.

27. The apparatus of claim 1 wherein the pump is positioned relatively near the fluid container.

28. The apparatus of claim 1 further in combination with a mechanism to move the agricultural crop relative to the apparatus and/or the apparatus relative to the agricultural crop.

29. The apparatus of claim 28 wherein the mechanism comprises a mechanical or pneumatic conveying system.

30. The apparatus of claim 28 wherein the mechanism comprises agricultural equipment.

31. The apparatus of claim 28 wherein the mechanism produces movement of agricultural crop relative to the apparatus at medium to relatively high speed.

32. The apparatus of claim 31 wherein the relatively high speed is of speeds up to 100 miles per hour.

33. The apparatus of claim 1 wherein the pump is reversible.

34. The apparatus of claim 1 further comprising a second container in fluid communication with the conduit.

35. The apparatus of claim 1 further comprising a second nozzle in fluid communication with the fluid conduit.

* * * * *